United States Patent [19]
Harder et al.

[11] Patent Number: 5,705,811
[45] Date of Patent: Jan. 6, 1998

[54] SYSTEM AND APPARATUS FOR CALIBRATING AN IMAGE DETECTOR

[75] Inventors: James A. Harder, Bedford; Keith A. Jacobson, Flower Mound; Val J. Herrera, Double Oak, all of Tex.

[73] Assignee: Raytheon TI Systems, Inc., Lewisville, Tex.

[21] Appl. No.: 741,875

[22] Filed: Oct. 30, 1996

[51] Int. Cl.$^6$ ................................................ H05H 3/02
[52] U.S. Cl. ............................ 250/252.1 A; 250/332
[58] Field of Search ..................... 250/252.1 A, 332, 250/347, 353

[56] References Cited

U.S. PATENT DOCUMENTS 5,422,485  6/1995  Bowids .............................. 250/252.1

*Primary Examiner*—Don Wong
*Attorney, Agent, or Firm*—Baker & Botts, L.L.P.

[57] ABSTRACT

A system (10) for calibrating an image detector includes a calibration platform (16) supporting a calibration element (18). The calibration element (18) may be made up of a first lens (20) and a second lens (22), each having a curved surface to appropriately alter characteristics of reference light levels (33) generated by a reference source (24). The second lens (22) may have its surface positioned differently to the focal plane array (14) than the first lens mirror (20) for enhanced calibration operation. The reference source (24) generates the reference light levels (33) over a range of temperatures to mimic the image energy generated by the scene (12). The reference source (24) may also include a reference lens element (26) that transmits reference light energy (33) generated by the reference source (24) or reflects scene base energy (34) generated by the scene (12) and allowed to pass through the first lens (20) and the second lens (22). The calibration platform (16) operates to position the first lens (20) and the second lens (22) in front of the focal plane array (14) during calibration operation and remove the first lens (20) and the second lens (22) from in front of the focal plane array (14) during normal image detection.

16 Claims, 1 Drawing Sheet

SYSTEM AND APPARATUS FOR CALIBRATING AN IMAGE DETECTOR

TECHNICAL FIELD OF THE INVENTION

The present invention relates in general to imaging detection technology and more particularly to a system and apparatus for calibrating an image detector.

BACKGROUND OF THE INVENTION

Calibration of focal plane arrays in image detection systems is necessary to adequately detect images within a scene. Typical opto-mechanical calibration techniques include using a shutter to flash in front of the focal plane array during calibration. The shutter may include a specific reference image such that the focal plane array detects a specific reference in order to calibrate its image sensing devices. The shutter may include a flat mirror such that the focal plane array detects itself for calibration purposes. The shutter/flat mirror technique only allows the focal plane array to calibrate on itself or a specific reference. Therefore, imaging system can benefit from improved opto-mechanical calibration schemes.

SUMMARY OF THE INVENTION

From the foregoing, it may be appreciated that a need has arisen for an improved and effective system and apparatus for calibrating an image detector. In accordance with the present invention, a system and apparatus for calibrating an image detector are provided that substantially eliminate or reduce disadvantages and problems associated with conventional image detector calibration techniques.

According to an embodiment of the present invention, there is provided a system for calibrating an image detector that includes a focal plane array operable to detect images from a scene. A reference source generates reference light levels to a movable calibration platform. The reference light levels are reflected/refracted/defracted from the movable calibration platform to the focal plane array. The movable calibration platform includes a calibration lens with a curved surface for reflecting/refracting/defracting the reference light levels.

The present invention provides various technical advantages over conventional image detector calibration techniques. For example, one technical advantage is to use a curved lens surface for calibration of a focal plane array. Another technical advantage is to allow scene based energy to be used in the calibration of the focal plane array. Yet another technical advantage is to generate reference light levels to mimic the scene energy in order to produce the calibration references that best match scene conditions. Still another technical advantage is to mix reference light levels with scene based energy for calibration of the focal plane array. Other technical advantages are readily apparent to one skilled in the art from the following figures, descriptions, and claims.

BRIEF DESCRIPTION OF THE DRAWINGS

For a more complete understanding of the present invention and the advantages thereof, reference is now made to the following description taken in conjunction with the accompanying drawings, wherein like reference numerals represent like parts, in which.

DETAILED DESCRIPTION OF THE INVENTION

Figure 1:
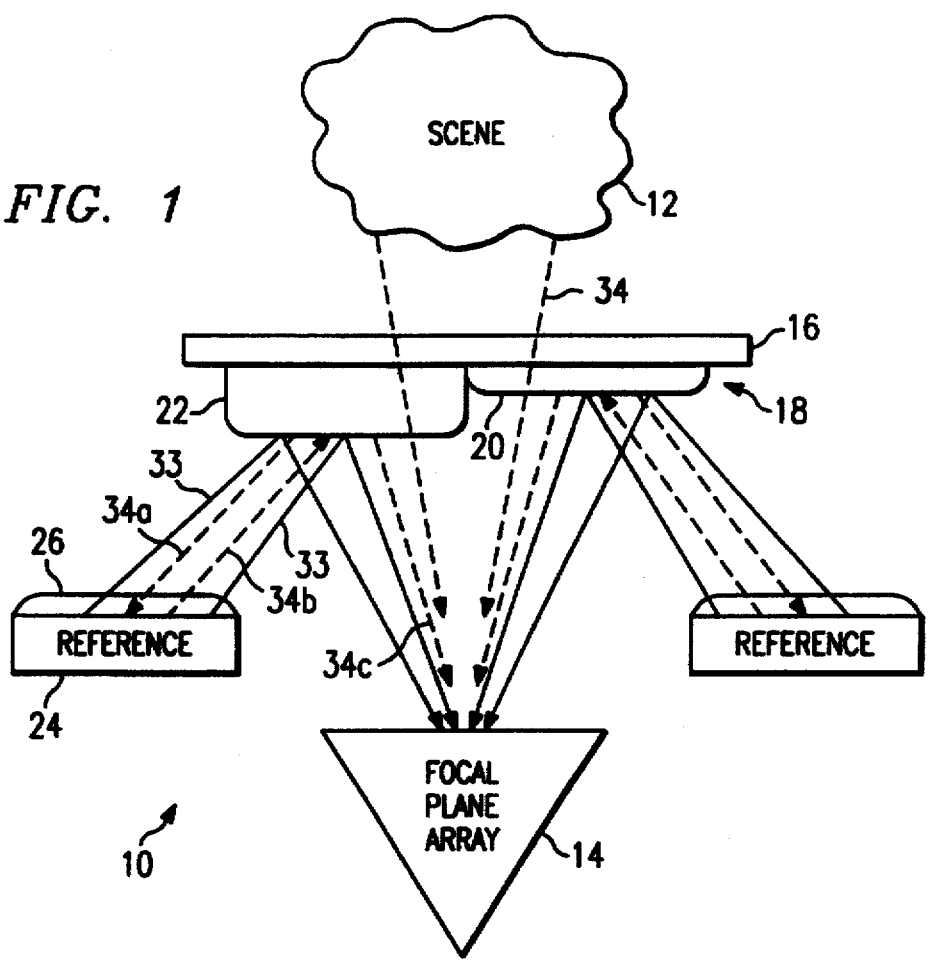
FIG. 1 illustrates a system for calibrating an image detector.

FIG. 1 is a simplified diagram of a system 10 for calibrating an image detector. System 10 receives energy from a scene 12 at a focal plane array 14. Focal plane array 14 processes energy received from scene 12 in order to detect an image of scene 12. System 10 also includes a calibration platform 16 that is positioned in front of focal plane array 14 for calibration of system 10. Calibration platform 16 includes a calibration element 18 having a first lens 20 and a second lens 22. System 10 also includes a reference source 24 that generates reference light levels for the calibration of focal plane array 14. Reference source 24 may also include a reference lens element 26 to control reference light levels generated by reference source 24. Reference lens element 26, first lens 20, and second lens 22 may have partial or total reflective surfaces, may be mirrors, or may allow partial or complete transmission of light depending upon the form of calibration desired.

For normal operation, calibration platform 16 is removed from in front of focal plane array 14 to allow focal plane array 14 to collect scene image levels 34 directly from scene 12. During calibration of system 10, calibration platform 16 is positioned in front of focal plane array 14. Reference source 24 is activated to generate reference light levels 33 that reflect from calibration element 18 for processing by focal plane array 14. Calibration platform 16 can be positioned in front of focal plane array 14 on a periodic or aperiodic basis to provide continuous or on demand calibration of focal plane array 14.

Reference source 24 may include a thermo-electric cooler/heater that can generate a range of temperatures to produce reference light levels 33. The temperature generated by reference source 24 may be passively set to a specific value or activity controlled to match the temperature at scene 12. The purpose of reference source 24 working in conjunction with calibration platform 16 is to apply passively and/or actively controlled spatially conditioned photons to focal plane array 14 and avoid photon gathering from unwanted places within system 10. Reference source 24 may implement reference lens element 26 to direct reference light levels 33 to calibration element 18.

Reference lens element 26 may direct scene image levels 34 (34a) refracted through calibration element 18 with a reflective surface back towards calibration element 18 (34b) for reflection to focal plane array 14 (34c). Reference lens element 26 may also allow transmission of reference light levels 33 therethrough as generated by reference source 24 for reflection from calibration element 18 to focal plane array 14. The net result of operating calibration element 18 with reference lens element 26 and reference source 24 is a temporal and spatially controlled mixing of scene energy 34 and reference energy 33. This mixing provides an optimized photon reference for focal plane array 14.

Figure 2:
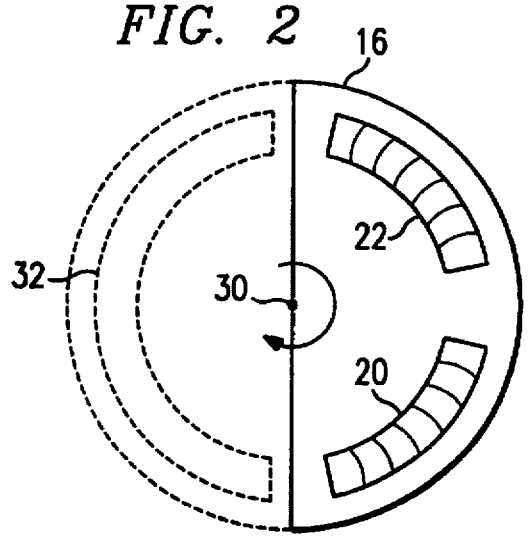
FIG. 2 illustrates a calibration platform for use in the image detector calibration system.

FIG. 2 is a simplified diagram of calibration platform 16. In this implementation, calibration platform 16 preferably rotates around an axis 30. Rotation of calibration platform 16 around axis 30 allows for the positioning of first lens 20 and second lens 22 in front of focal plane array 14 during calibration. For image detection, calibration platform 16 rotates to remove first lens 20 and second lens 20 from in front of focal plane array 14. Though shown as a half disk, calibration platform 16 may have a full disk configuration as indicated by the dashed lines with an aperture 32 that can be rotated to a position in front of focal plane array 14 for image detection operation.

First lens 20 and second lens 22 preferably have curved surfaces in order to alter the characteristic of reference light levels 33 generated by reference source 24. The curved surfaces of first lens 20 and second lens 22 are selected to appropriately alter the characteristics of reference light levels 33 reflected toward focal plane array 14. In addition to reflecting reference light levels 33 from reference source 24, first lens 20 and second lens 22 may allow energy 34 from scene 12 to be applied directly to focal plane array 14 and/or indirectly by reflection from reference lens element 26 at reference source 24. In this manner, scene based energy 34 may be used for the calibration of focal plane array 14. Further, first lens 20 may have its surface spaced from focal plane array 14 at a different distance and orientation than the surface of second lens 22. Different displacements of first lens 20 and second lens 22 from focal plane array 14 provide different and additional parameters for calibration of focal plane array 14.

Opto-mechanical characteristics of first lens 20 and second lens 22 may be altered in order to affect an amount of transmittance or reflectance of scene based energy 34 and/or reference light levels 33. Opto-mechanical characteristics include different lens orientations, selective coating on the lenses, and selective patterning of the lenses. With changes to the opto-mechanical characteristics of the lenses, variable mixing of scene based energy 34 and reference light levels 33 may be achieved for selective calibration performance.

In summary, a system for calibrating an image detector includes a calibration platform having a calibration lens element made up of a first lens and a second lens. The first lens and the second lens direct reference light levels generated by a reference source to a focal plane array in order to calibrate the focal plane array. The first lens and the second lens have curved surfaces with selected transmittance and reflectance levels to alter the characteristics of the reference light levels for appropriate calibration purposes. The first lens and the second lens may have surfaces at different distances and orientations to the focal plane array. The reference source generates reference light levels through a range of different temperatures or through reflection and transmission by a reference lens element. The calibration platform positions the calibration lens element in front of the focal plane array during calibration operation and removes the calibration lens element from in front of the focal plane array during image detection of a scene.

Thus, it is apparent that there has been provided, in accordance with the present invention, a system for calibrating an image detector that satisfies the advantages set forth above. Although the preferred embodiment has been described in detail, it should be understood that various changes, substitutions, and alterations can be made herein. For example, though the calibration platform is shown to rotate the first lens and the second lens into position for calibration purposes, the first and second lenses may be positioned in front of the focal plane array by a variety of placement techniques not limited by rotary motion. Other examples are readily ascertainable by one skilled in the art and may be made without departing from the spirit and scope of the present invention as defined by the following claims.

What is claimed is:

1. A system for calibrating an image detector, comprising:
a focal plane array operable to detect images from a scene;
a reference source operable to generate reference light levels;
a movable calibration platform operable to reflect said reference light levels generated by said reference source to said focal plane array, said movable calibration platform including a calibration element with a curved surface for reflecting said reference light levels.

2. The system of claim 1, wherein said reference source generates any of a plurality of temperatures to provide said reference light levels.

3. The system of claim 2, wherein said reference source generates a temperature to match a temperature of said scene.

4. The system of claim 1, wherein said reference source is a reference lens element operable to provide said reference light levels to said movable calibration platform.

5. The system of claim 1, wherein said calibration element includes a first lens and a second lens, said second lens being spatial positioned differently to said focal plane array than said first lens.

6. The system of claim 1, wherein said calibration element allows a portion of energy from said scene to be applied to said focal plane array.

7. The system of claim 6, wherein energy from said scene is mixed with said reference light levels, said reference light levels adjusted to provide an optimized photon reference for said focal plane array in response to said scene based energy.

8. The system of claim 6, wherein said reference source reflects energy from said scene for reflection to said focal plane array by said calibration element.

9. The system of claim 1, wherein said calibration element includes a mirror.

10. The system of claim 1, wherein said movable calibration platform is operable to position said calibration element in front of said focal plane array for calibration of said focal plane array, said movable calibration platform operable to remove said calibration element from in front of said focal plane array to allow said focal plane array to collect image information from said scene.

11. The system of claim 10, wherein said movable calibration platform is periodically or aperiodically position in front of said focal plane array for continuous or on demand calibration of said focal plane array during intervals in collection of image information from said scene.

12. A system for calibrating an imaging detector, comprising:
a focal plane array operable to detect images from a scene;
a reference source operable to generate reference light levels, said reference source including a thermoelectric heater/cooler to provide a range of heated and cooled temperatures to said reference light levels;
a rotatable calibration platform operable to reflect said reference light levels generated by said reference source to said focal plane array, said rotatable calibration platform including a first lens and a second lens each with a curved surface for reflecting said reference light levels, said curved surface of said second lens being spatially aligned different to said focal plane array than said curved surface of said first lens, said focal plane array collecting said reference light levels from said first and second lenses for calibration purposes, said first and second lenses each having a radius of curvature selected to alter characteristics of said reference light levels for desired calibration adjustments to said focal plane array.

13. The system of claim 12, wherein said first lens directs a portion of energy from said scene to said focal plane array.

14. The system of claim 13, wherein said reference source includes a lens element that reflects scene based light energy to said calibration platform.

15. The system of claim 12, wherein said first lens has a partially or totally reflective surface.

16. The system of claim 12, wherein said calibration platform is operable to position said first and second lenses in front of said focal plane array for calibration of said focal plane array, said calibration platform operable to remove said first and second lenses from in front of said focal plane array to allow said focal plane array to collect image information from said scene.

* * * * *